(12) United States Patent
Doerr et al.

(10) Patent No.: US 11,583,686 B2
(45) Date of Patent: Feb. 21, 2023

(54) BATTERY WITH INTEGRATED ELECTRONIC MODULE

(71) Applicant: BIOTRONIK SE & CO. KG, Berlin (DE)

(72) Inventors: Thomas Doerr, Berlin (DE); Tim Traulsen, Pirna (DE); Torsten Oertmann, Blankenfelde (DE); Gregory Jay Delmain, Tualatin, OR (US); Alan Fryer, Portland, OR (US)

(73) Assignee: BIOTRONIK SE & Co. KG, Berlin (DE)

( * ) Notice: Subject to any disclaimer, the term of this patent is extended or adjusted under 35 U.S.C. 154(b) by 370 days.

(21) Appl. No.: 16/993,427

(22) Filed: Aug. 14, 2020

(65) Prior Publication Data
US 2021/0052904 A1    Feb. 25, 2021

Related U.S. Application Data

(60) Provisional application No. 62/888,549, filed on Aug. 19, 2019.

(30) Foreign Application Priority Data
Sep. 13, 2019    (EP) .................................... 19197335

(51) Int. Cl.
| A61N 1/378 | (2006.01) |
| A61N 1/362 | (2006.01) |
| A61N 1/375 | (2006.01) |
| A61N 1/372 | (2006.01) |
| A61N 1/39 | (2006.01) |
| H01M 10/42 | (2006.01) |
(Continued)

(52) U.S. Cl.
CPC ............. *A61N 1/378* (2013.01); *A61N 1/362* (2013.01); *A61N 1/37211* (2013.01); *A61N 1/37512* (2017.08); *A61N 1/3956* (2013.01); *A61N 1/39622* (2017.08); *H01G 11/32* (2013.01); *H01G 11/46* (2013.01); *H01G 11/80* (2013.01); *H01M 10/425* (2013.01); *H01M 10/46* (2013.01); *H01M 50/116* (2021.01); *H01M 2220/30* (2013.01)

(58) Field of Classification Search
CPC ...... A61N 1/378; A61N 1/3975; A61N 1/375; A61N 1/37512
See application file for complete search history.

(56) References Cited

U.S. PATENT DOCUMENTS

2002/0051550 A1   5/2002   Leysieffer
2006/0222942 A1*  10/2006  Zhao ................. H01M 10/0585
                                                    429/180

FOREIGN PATENT DOCUMENTS

EP    0801958 A1   10/1997
EP    1507306 A1    2/2005
(Continued)

*Primary Examiner* — Brian T Gedeon
(74) *Attorney, Agent, or Firm* — Laurence A. Greenberg; Werner H. Stemer; Ralph E. Locher

(57) ABSTRACT

An implantable medical device contains a hermetic battery. The hermetic battery contains a hermetically sealed battery housing defining an internal chamber, an electrochemical cell disposed within the internal chamber, and an electronic module disposed within the internal chamber. The electronic module is electrically conductively connected to the electrochemical cell, and the electronic module is arranged in the electrochemical cell.

20 Claims, 3 Drawing Sheets

(51) Int. Cl.
*H01M 50/116* (2021.01)
*H01G 11/32* (2013.01)
*H01G 11/46* (2013.01)
*H01G 11/80* (2013.01)
*H01M 10/46* (2006.01)

(56) References Cited

FOREIGN PATENT DOCUMENTS

| WO | 2009120483 A1 | 10/2009 |
| WO | 2016140873 A1 | 9/2016 |

\* cited by examiner

BATTERY WITH INTEGRATED ELECTRONIC MODULE

CROSS-REFERENCE TO RELATED APPLICATION

This application claims priority, under 35 U.S.C. § 119, of US provisional patent application U.S. 62/888,549, filed Aug. 19, 2019 and of European patent application EP 19197335, filed Sep. 13, 2019; the prior applications are herewith incorporated by reference in their entireties.

BACKGROUND OF THE INVENTION

Field of the Invention

The present disclosure relates to a battery with an integrated electronic module and to an implantable medical device comprising such a battery.

Medical implant designs, particularly regarding pacemakers and cardioverter defibrillators, constantly evolve toward lower volume solutions. Design efforts aim towards a reduction of the number of components, improved packing efficiency of the components, power reduction leading to reduced battery volume, or improved battery volumetric efficiency.

However, existing solutions for improving packing efficiency are limited by packing generally rectangular components into medical implant housings which tend toward rounded designs. Also, the various components sometimes have different heights and must be placed on a substrate which provides mechanical stability and electrical connectivity. This all leads to packing inefficiency due to unused spaces left around the components.

BRIEF SUMMARY OF THE INVENTION

Based on this background, it is an objective to provide an efficient design of a medical implant, particularly of its components, in which the number of components is reduced, the volume of the implant is more efficiently used and which enables a less laborious manufacturing.

This objective is solved by an implantable medical device having the features of the independent claim. Appropriate embodiments thereof are stated in the dependent claims and the description below.

In one aspect, an implantable medical device is provided, which comprises a hermetic battery. The hermetic battery comprises:
a) a hermetically sealed battery housing defining an internal chamber,
b) an electrochemical cell comprised within the internal chamber, and
c) an electronic module comprised within the internal chamber.

The electronic module is electrically conductively connected to the electrochemical cell and the electronic module is arranged in the electrochemical cell.

The electronic module and the electrochemical cell may be non-hermetically separated from each other. The housing of the implantable medical device may be completely formed by the battery housing.

Advantageously, the number of components of the implantable medical device is significantly reduced in the medical device of the invention compared to common devices, since only one hermetically sealed housing and particularly only one hermetically sealed feedthrough are necessary. Accordingly, manufacturing is significantly simplified.

In another aspect, an hermetic battery is provided, which comprises:
a) a hermetically sealed battery housing defining an internal chamber,
b) an electrochemical cell comprised within the internal chamber, and
c) an electronic module comprised within internal chamber.

The electronic module is electrically conductively connected to the electrochemical cell and the electronic module is arranged in the electrochemical cell.

Particularly, it is envisioned according to the invention that the electronic module is configured to generate an electric pulse, particularly a therapeutic electric pulse, and/or to determine a physiological parameter, particularly one or more physiological electric pulses, e.g. from the heart tissue of a patient, e.g. an electrocardiogram.

In some embodiments of the implantable medical device of the invention, the electronic module comprises a pulse generating unit being able to generate the (therapeutic) electric pulse.

In some embodiments of the implantable medical device or the hermetic battery, the hermetically sealed battery housing comprises a hermetically sealed feedthrough, wherein the electronic module is electrically conductively connected to the feedthrough.

In some embodiments of the implantable medical device, the hermetically sealed battery housing forms at least partly, preferably completely, the housing of the implantable medical device.

Particularly, the battery housing and the feedthrough are configured to hermetically seal the internal chamber, particularly such that substances of the battery do not leak out of the battery housing or that substances from outside of the housing do not leak into the battery housing. This can be achieved, for example, by a battery housing made of a metal or metal alloy, and a feedthrough comprising a metal flange, which is welded into a matching recess or opening of the battery housing. Particularly, the feedthrough may comprise one or more electrically conductive connecting elements surrounded by an isolation body, respectively, which are fixed into matching openings in a metal flange, particularly by soldering, brazing or welding, which is in turn soldered, brazed or welded to the housing, thereby yielding a hermetically sealed feedthrough and a hermetically sealing battery housing. The battery housing may be formed by two half shells welded together or by a housing beaker, for example a deep-drawn beaker, and a corresponding cover or lid welded together.

Typically, the feedthrough of an implantable medical device such as a pacemaker, a cardioverter defibrillator or neurostimulator is connected to electrical contact elements comprised in a so called header assembly, which provide a means to transmit electronic signals from the electronic module and/or the electrochemical cell via the feedthrough, particularly the connecting element, to a lead, which conducts the intended therapy. The header assembly, more specifically the electrical contact elements are typically configured to receive a connector of the above mentioned lead.

In some embodiments of the implantable medical device or the hermetic battery, the electrochemical cell comprises at least a first electrolyte, wherein the electronic module is in fluid communication with the at least first electrolyte.

In some embodiments of the implantable medical device or the hermetic battery, the battery housing is made of a biocompatible material.

In some embodiments of the implantable medical device or the hermetic battery, the battery housing is made of a biocompatible metal or metal alloy, and the electrochemical cell is electrically isolated from the battery housing. Particularly, the battery housing is made of titanium or a titanium alloy.

In some embodiments of the implantable medical device or the hermetic battery, the electrochemical cell is at least partly comprised within an envelope made of an electrically insulating material. Particularly, the electrically insulating material is PEEK (polyether ether ketone, CAS Nr. 29658-26-2), POM (polyoxymethylene, CAS No. 9002-81-7), a parylene, a silicone or other polyimide based materials.

In some embodiments of the implantable medical device or the hermetic battery, the electronic module is at least partly, particularly completed, covered with a protective layer or embedded within a protective cover. The term "protective layer" or protective cover" in the context of the present specification particularly refers to a layer or cover that comprises a compound that is resistant or chemically inert to the condition of the electrochemical cell, particularly, resistant or chemically inert to an electrolyte comprised within the electrochemical cell.

In some embodiments of the implantable medical device or the hermetic battery, the electronic module is at least partly, particularly completely, covered with a parylene (a poly(p-xylylene) polymer). Non-limiting examples for a parylene include parylene C, parylene N, parylene D and parylene HT.

In some embodiments of the implantable medical device or the hermetic battery, the electronic module is at least partly, particularly complete, covered with or embedded within a liquid crystal polymer like poly(p-phenyleneterephthalamide (Kevlar), Vectran (a polycondensation product of 4-hydroxybenzoic acid and 6-hydroxynaphthalene-2-carboxylic acid) or Zenite (a liquid crystal polymer with glass fiber filler).

In some embodiments of the implantable medical device or the hermetic battery, the electronic module is at least partly, particularly complete, covered with or embedded within an epoxy resin. Particular suitable epoxy resins include, without being restricted to, Vitralit (which is a cationic one component epoxy resin curable by UV radiation) and Structalit (which can be a one or two component epoxy resin curable by heat), both also known as Glob-top casting compounds.

In some embodiments of the implantable medical device or the hermetic battery, the electronic module comprises one or more circuits, particularly one or more integrated circuits. Particularly, the electronic module comprises a microprocessor and/or a storage component.

In some embodiments of the implantable medical device or the hermetic battery, the electronic module comprises a pulse generating unit or circuit, particularly a pacing unit or circuit and/or a shock unit or circuit, being able to generate the (therapeutic) electric pulse.

In some embodiments of the implantable medical device or the hermetic battery, the electronic module, particularly the pacing unit or circuit, is configured to provide a low voltage pulse, particularly a series of low voltage pulses, for example with a voltage in the range of 1.0 to 7.5 V.

In some embodiments of the implantable medical device or the hermetic battery, the electronic module, particularly the shock unit or circuit, is configured to provide a high voltage pulse, particularly with a voltage in the range of 100 to 1200 V. The electronic module may be connected to a capacitor, and the capacitor may be charged and discharged with the high voltage pulse, e.g. in the range of 100 to 1200 V.

In some embodiments of the implantable medical device or the hermetic battery, the electronic module further comprises a diagnostic unit or circuit, a telemetry unit or circuit and/or a charge control unit or circuit.

In some embodiments of the implantable medical device or the hermetic battery, the electronic module is configured to determine, particularly measure, one or more of the following physiological functions or parameters: electrocardiogram, electroencephalogram, temperature, pressure, pH, acceleration, sound, a concentration of physiological compound or metabolite, e.g. glucose, oxygen, carbon dioxide or the like.

In some embodiments of the implantable medical device or the hermetic battery, the hermetic battery further comprise at least one capacitor, wherein preferably the capacitor is electrically connected to the electrochemical cell and/or the electronic module.

In some embodiments of the implantable medical device or the hermetic battery, the hermetic battery is a primary battery or a secondary battery.

In some embodiments of the implantable medical device or the hermetic battery, the electronic module comprises a self-test unit or circuit, wherein the self-test unit or circuit is configured to conduct a burn-in test and/or a function test of the electronic module and, wherein the self-test module is configured to transmit results of the burn-in test and/or the function test. Such burn-in test may be performed at an increased temperature and under defined load conditions including monitoring of electrical parameters like battery voltage, impedance, etc.

In some embodiments of the implantable medical device or the hermetic battery, the hermetically sealed battery housing comprises a hermetically sealable opening. Advantageously, an electrolyte may be filled into the electrochemical cell via the hermetically sealable opening. After filling the electrolyte into the electrochemical cell, the hermetically sealable opening may be hermetically sealed, e.g. by welding.

Accordingly in some embodiments of the implantable medical or the hermetic battery, the electrochemical cell comprises at least a first cathode and at least a first anode, but not an electrolyte.

In some embodiments of the implantable medical device or the hermetic battery, the electrochemical cell comprises at least a first anode made of a material consisting of or comprising, but not being restricted to, lithium, graphites, hard carbon, meso-carbon, silicon, and/or lithium-titanate.

In some embodiments of the implantable medical device or the hermetic battery, the electrochemical cell comprises at least a first cathode made of a material consisting of or comprising, but not being restricted to, manganese oxide, vanadium oxide, carbon monofluoride, lithium cobalt oxide or a mixed metal oxide.

In some embodiments of the implantable medical device or the hermetic battery, the electrochemical cell comprises at least a first electrolyte consisting of or comprising, but not being restricted to, a non-aqueous or aqueous solvent with dissolved salts, particularly dissolved salts of lithium like lithium perchlorate, lithium hexafluorophosphate, lithium hexafluoroarsenate or lithium tetrafluoroborate.

In some embodiments of the implantable medical device or the hermetic battery, the electronic module at least partly electrically isolates the electrochemical cell from the battery housing, wherein particularly the electronic module is arranged between the electrochemical cell and the feedthrough.

In some embodiments of the implantable medical device or the hermetic battery, the electronic module comprises a power-on unit, which is configured to control a defined start up procedure during filling the electrolyte into the battery. Advantageously, the hermetic battery or the implantable medical device of the invention may be premanufactured and stored without consumption of the battery charge. Such power-unit may be formed by a management circuitry, which monitors the battery voltage and manages the power on of the complete system by using voltage regulators etc.

In some embodiments of the implantable medical device, the device further comprises a connector assembly being electrically conductively connected to the hermetically sealed feedthrough outside of the hermetically sealed battery housing, particularly to one or more connecting elements of the hermetically sealing feedthrough. Particularly, such connector may comprise two or more electrical connecting elements, such as, for example, a spring sleeve or an annular member with a fixed spring element or a socket, that are configured to conductively connect a connector of a lead received by the connector assembly to the hermetically feedthrough and ultimately to the electronic module and the electrochemical cell. This may be facilitated by ribbons welded to the connecting element of the feedthrough and the connecting element of the connector assembly. Particularly, the connector assembly comprises two, four or eight connecting elements. Typically, a biocompatible resin, commonly an epoxy resin, is then casted around the connector assembly.

In some embodiments of the implantable medical device, the implant comprises a capacitor, particularly a by-pass capacitor, comprised within the internal chamber. Particularly, the capacitor, particularly the by-pass capacitor, is encased or embedded in aluminium oxide, e. g, sapphire.

Accordingly one embodiment, an integrated circuit or other components, substantially hermetically sealed, are placed within an electrochemical cell, where some components previously realized as discrete components are now realized on the integrated circuit. Accordingly, as many components as possible are transferred onto or arranged on the silicon die of the controlling integrated circuit. The integrated circuit is preferably encased in aluminum oxide (sapphire) and placed within the electrolyte of the electrochemical cell thus eliminating useless volume between components. A bypass capacitor could also be placed in the cell to improved high frequency current demand. Also, an antenna coil in the form of an insulted platinum coil could be located within the cell. Remaining components would have to be located outside the cell, requiring feedthrough connections so these would have to be minimized.

Advantageously, a volumetric efficiency improvement from incorporating small capacitors on an integrated circuit (IC) is possible because they have very low profile on an integrated circuit, and by placing the integrated circuit within the cell chemistry, all volume around the IC is efficiently used to increase the capacity of the cell. This embodiment works best for cases of a lone signal leaving the integrated circuit through a feedthrough.

According to an alternative embodiment, an integrated circuit and other low profile components are contained in a low profile ceramic package, which is then placed within an electrochemical cell, wherein the ceramic package provides electrical feedthrough to the exterior of the cell. Particularly, a ceramic substrate with a cavity and lid to contain low profile components is utilized within the electrochemical cell and provide a hermetic enclosure. An extension of this substrate would contain conductors on inner layers and pass through a glass frit or other sealing mechanism to act as a feedthrough to exit the cells interior. Necessary external components could be placed on this feedthrough exterior to the cell.

Advantageously, the disclosed feedthrough technique solves electrical isolation issues associated with signals leaving the IC. The second embodiment is less limited.

Other features which are considered as characteristic for the invention are set forth in the appended claims.

Although the invention is illustrated and described herein as embodied in a battery with an integrated electronic module, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Generally, the present disclosure aims towards limiting the number of external components and using the entire volume around the limited components to increase the storage capacity of the electrochemical cell of a battery.

Figure 1:
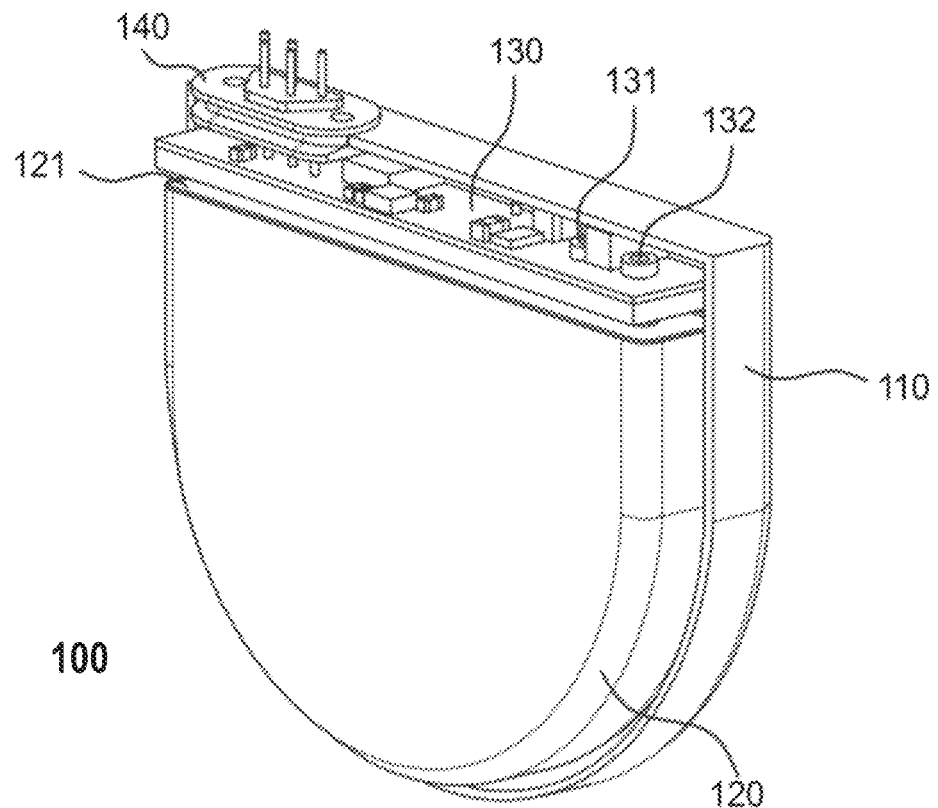
FIG. 1 is a diagrammatic, perspective view of an implantable cardioverter defibrillator according to the prior art.

Referring now to the figures of the drawings in detail and first, particularly to FIG. 1 thereof, there is shown the design of a conventional implantable active medical device such as a pacemaker (IPG) 100. The pacemaker comprises a first hermetically closed housing 110 made of a biocompatible material (commonly case titanium or a titanium alloy), in which comprises a battery 120, an electronic module 130 and electric through-connections comprised within via a hermetically sealing feedthrough, which are designed to connect the electronic module 130 with one or more components outside of the closed housing 110 commonly known as the header of the pacemaker (not shown in FIG. 1). Such a header usually comprises one or more connector assemblies that are configured to receive one or more leads of the pacemaker. The battery 120 comprises a second hermetically sealed battery housing 121 to protect the electronic module 130 from the interior of the battery 120, i.e. the environment or the electrolyte within the battery, respectively. The electric connection between the battery and the electronic module is realized by two battery terminals 131, 132. Those terminals 131, 132 likewise are guided out of the battery housing 121 via a feedthrough.

Figure 2:
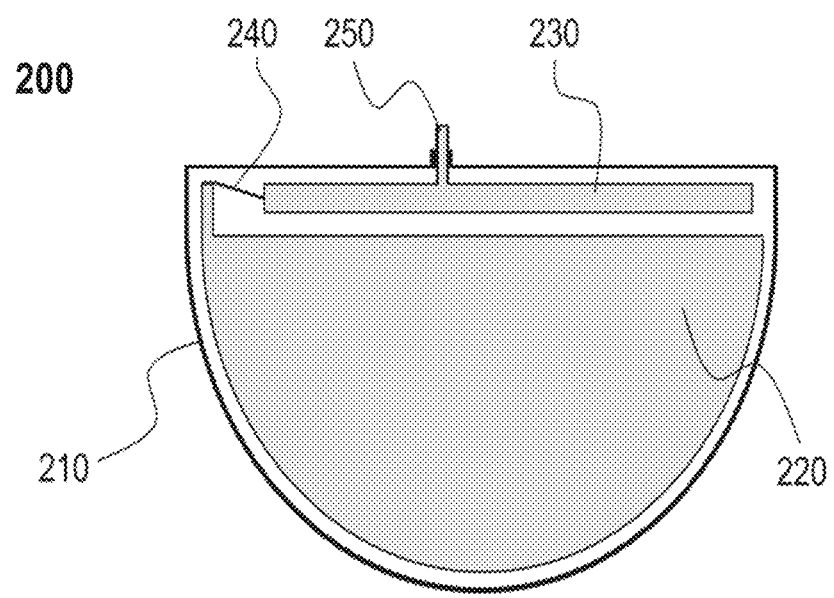
FIG. 2 is a top plan view of an embodiment of the implantable device according to the invention.

FIG. 2 shows the more convenient, improved pacemaker design 200 according to the invention. The pacemaker 200 comprises a single hermetically sealed biocompatible housing 210, in which the components of the battery 220 (anode, cathode, electrolyte) are accommodated and additionally the electronic module 230. The electronic module 230 is preferably coated, for example with a parylene, to protect the electronic module 230 from the conditions present inside the battery. The electronic module 230 is connected inside the battery connected to the power or voltage supply via an electrical connection 240. For connecting the electronic module 230 with the outer components of the pacemaker, i.e. the lead via the header, a terminal of the electronic module 230, e.g. a stimulating terminal, is guided through the housing 220 by a hermetically sealed feedthrough 250.

By the design of the invention, the engineering effort is significantly reduced, particularly since only one hermetically sealed housing and one hermetically sealed feedthrough are needed. Advantageously, the above described design is applicable for any implantable medical device, such as a cardiac monitors, or active implants besides pacemakers such as neurostimulators or cardioverter defibrillators.

Figure 3:
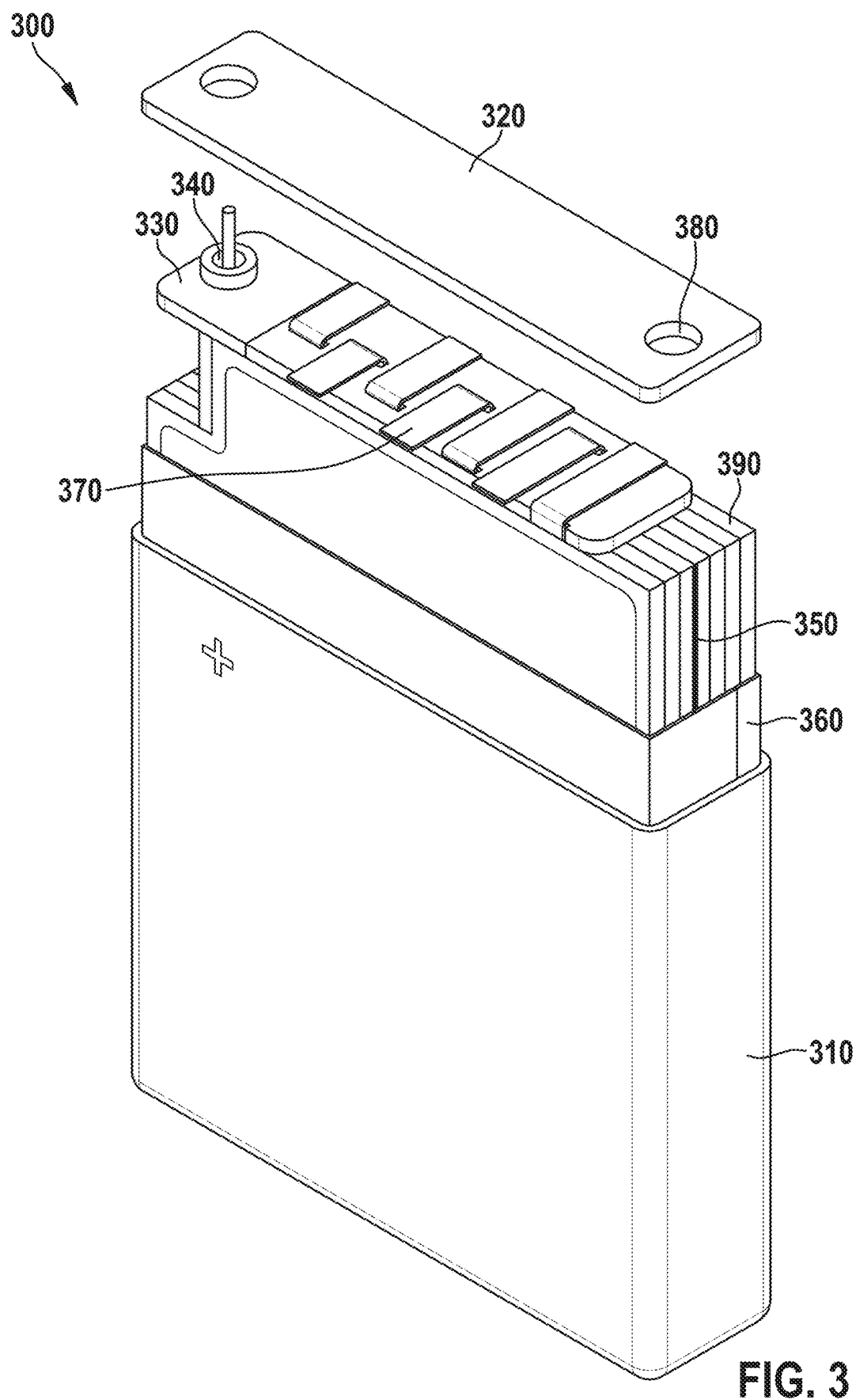
FIG. 3 is a perspective view of an alternative embodiment of the implantable device according to the invention.

FIG. 3 shows another design of the invention comprising a battery according to the invention with an integrated electronic module. The depicted active implant 300 comprises a housing 310 or housing beaker made of titanium that is hermetically sealable with a cover element 320 of the housing. An encapsulated electronic module 330 is integrated in the housing 310 such that it is sufficiently protected against the conditions present within the housing. The electronic module 330 is equipped with or connected to a feedthrough 340, by which one or more terminals for leads, sensors, antenna, etc., may be electrically guide through the cover element 320 in a hermetically tight manner. Typically, such feedthrough 340 comprise one or more connecting elements such as conductive pin that are isolated from a flange or the cover element by an insulating element such as glass, ceramic or a polymer such as an epoxy resin.

Also electrodes 360 of the battery (i. e. the electrode package including anodes, cathodes and separators, etc.) are integrated into the housing 310 and insulated from the housing 310 or housing beaker by an insulating envelope. Advantageously, insulating the electrodes 360 against the cover element 320 can be constructively realized by the electronic module 330, particularly by arranging the electronic module between the electrodes 350 and the cover element 320 as illustrated in FIG. 3. Additionally, the electronic module 330 is used to electrically interconnect the common arrestors of the electrodes, respectively.

For filling the housing 310 with an appropriate electrolyte, the cover element 320 may comprise an opening 380 through which the electrolyte may be filled into the housing and which will be hermetically closed after filling. To enable the flow of the electrolyte, the electronic module 330 is designed shorter than the front side 370 of an electrode package 360.

The invention claimed is:

1. An implantable medical device, comprising:
a hermetic battery, said hermetic battery containing:
a hermetically sealed battery housing defining an internal chamber;
an electrochemical cell disposed within said internal chamber; and
an electronic module disposed within said internal chamber,
wherein said electronic module is configured to generate a therapeutic electric pulse, and/or to determine a physiological parameter, wherein said electronic module is electrically conductively connected to said electrochemical cell, and said electronic module is disposed in said electrochemical cell.

2. The implantable medical device according to claim 1, wherein said hermetically sealed battery housing is made of a biocompatible material.

3. The implantable medical device according to claim 1, wherein said hermetically sealed battery housing is made of a biocompatible metal or metal alloy, and said electrochemical cell is electrically isolated from said hermetically sealed battery housing.

4. The implantable medical device according to claim 1, wherein said electrochemical cell is at least partly formed within an envelope made of an electrically isolating material.

5. The implantable medical device according to claim 1, wherein said electronic module is at least partly covered by a protective layer or embedded within a protective cover.

6. The implantable medical device according to claim 1, wherein said electronic module contains at least one circuit.

7. The implantable medical device according to claim 1, wherein said electronic module contains a pulse generating unit being able to generate said therapeutic electric pulse.

8. The implantable medical device according to claim 6, wherein:
said electronic module is configured to provide a low voltage pulse with a voltage in a range of 1.0 to 7.5 V; and/or
said electronic module is configured to provide a high voltage pulse in a range of 100 to 1200 V.

9. The implantable medical device according to claim 1, wherein said electronical module contains a diagnostic unit, a telemetry unit and/or a charge control unit.

10. The implantable medical device according to claim 1, wherein said hermetic battery further has at least one capacitor.

11. The implantable medical device according to claim 1, wherein said electronic module has a self-test module configured to conduct a burn-in test and/or a function test of said electronic module and, wherein said self-test module is further configured to transmit results of the burn-in test and/or the function test.

12. The implantable medical device according to claim 1, wherein said hermetically sealed battery housing has a hermetically sealable opening formed therein.

13. The implantable medical device according to claim 1, wherein said electrochemical cell contains:
at least a first anode essentially consisting of or comprising lithium, graphites, hard carbon, meso-carbons, silicium, and/or lithium-titanate; and/or
at least a first cathode essentially consisting of or comprising manganese oxide, vanadium oxide, carbon monofluoride, a lithium cobalt oxide or a mixed metal oxide; and/or
an electrolyte essentially consisting of or comprising a non-aqueous or aqueous solvent with dissolved salts selected from the group consisting of lithium perchlorate, lithium hexafluorophosphate, lithium hexafluoroarsenate and lithium tetrafluoroborate.

14. The implantable medical device according to claim 1, wherein said electronic module at least partly electrically isolates said electrochemical cell from said hermetically sealed battery housing.

15. The implantable medical device according to claim 1, wherein the physiological parameter is a physiological electric pulse.

16. The implantable medical device according to claim 3, wherein said biocompatible metal or said metal alloy includes titanium.

17. The implantable medical device according to claim 4, wherein said electrically isolating material is formed from polyetheretherketone, polyoxymethylene, a parylene or other polyimide based materials.

18. The implantable medical device according to claim 1, wherein said electronic module is completely covered by a protective layer or embedded within a protective cover.

19. The implantable medical device according to claim 6, wherein said at least one circuit is an integrated circuit, a microprocessor and/or a storage component.

20. The implantable medical device according to claim 7, wherein said pulse generating unit is a pacing unit and/or a shock unit.

* * * * *